United States Patent [19]

Moeller et al.

[11] Patent Number: 5,611,817
[45] Date of Patent: Mar. 18, 1997

[54] ISATIN DERIVATIVES FOR COLORING KERATIN-CONTAINING FIBERS

[76] Inventors: Hinrich Moeller, Haydnstr. 27, 40789 Monheim; Horst Hoeffkes, Carlo-Schmid-Str. 113, 40595 Duesseldorf, both of Germany

[21] Appl. No.: 535,263

[22] PCT Filed: Apr. 21, 1994

[86] PCT No.: PCT/EP94/01247

§ 371 Date: Oct. 30, 1995

§ 102(e) Date: Oct. 30, 1995

[87] PCT Pub. No.: WO94/24989

PCT Pub. Date: Nov. 10, 1994

[30] Foreign Application Priority Data

Apr. 30, 1993 [DE] Germany .......... 43 14 318.0

[51] Int. Cl.⁶ ..................... A61K 7/13
[52] U.S. Cl. ............... 8/405; 8/409; 8/423; 8/574
[58] Field of Search .............. 8/405, 406, 409, 8/423, 574, 416, 421; 548/485

[56] References Cited

U.S. PATENT DOCUMENTS

| | | | |
|---|---|---|---|
| 4,750,908 | 6/1988 | Rosenbaum et al. | 8/405 |
| 4,921,503 | 5/1990 | Anderson et al. | 8/405 |
| 5,190,564 | 3/1993 | Lang et al. | 8/423 |
| 5,261,926 | 11/1993 | Lang et al. | 8/405 |
| 5,279,616 | 1/1994 | Lang et al. | 8/406 |
| 5,340,366 | 8/1994 | Lang et al. | 8/423 |

FOREIGN PATENT DOCUMENTS

| | | |
|---|---|---|
| 0359465 | 3/1990 | European Pat. Off. . |
| 369344 | 5/1990 | European Pat. Off. . |
| 0497697 | 8/1992 | European Pat. Off. . |
| 0502783 | 9/1992 | European Pat. Off. . |
| 0502784 | 9/1992 | European Pat. Off. . |
| 3635147 | 4/1987 | Germany . |
| 2231414 | 9/1990 | Japan . |
| 9319725 | 10/1993 | WIPO . |

OTHER PUBLICATIONS

"High Pressure Liquid Chromatographic Determination of Intermediates and Subsidiary Colors in FD&C Blue No., 2", J.E. Bailey, J. Assoc. Off. Anal. Chem., 1980, Abstract only.

*Primary Examiner*—Paul Lieberman
*Assistant Examiner*—Caroline L. Dusheck
*Attorney, Agent, or Firm*—Ernest G. Szoke; Wayne C. Jaeschke; Real J. Grandmaison

[57] ABSTRACT

A process for coloring keratin-containing fibers by contacting the fibers with a composition containing an isatin derivative corresponding to formula I:

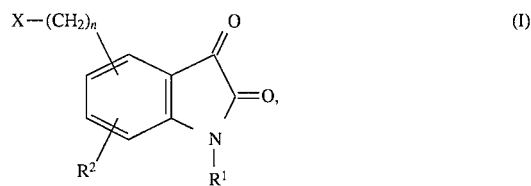

wherein $R^1$ is hydrogen, a $C_{1-4}$ alkyl group, a $C_{2-4}$ hydroxyalkyl group, a $C_{2-20}$ acyl group, a benzyl or phenyl group, $R^2$ is hydrogen, a $C_{1-4}$ alkyl group, a $C_{1-4}$ alkoxy group, a hydroxy, halogen or nitro group, X is a sulfo group —$SO_3H$ or a carboxyl group —COOH and n is an integer from 0 to 3, including water-soluble salts thereof.

20 Claims, No Drawings

ISATIN DERIVATIVES FOR COLORING KERATIN-CONTAINING FIBERS

BACKGROUND OF THE INVENTION

1. Field of the Invention

This invention relates to the use of certain isatin derivatives containing sulfo groups or carboxyl groups for coloring keratin-containing fibers and to coloring formulations containing these isatin derivatives.

Keratin-containing fibers, for example hair, wool or furs, are generally colored either with substantive dyes or with oxidation dyes which are formed by oxidative coupling of one or more primary intermediates with one another or with one or more secondary intermediates. Although intensive colors with good fastness properties can be obtained with oxidation dyes, development of the color takes place under the effect of oxidizing agents, such as $H_2O_2$ for example, which frequently results in damage to the fibers. Although substantive dyes are applied under more moderate conditions, their disadvantage is that the colors often have unsatisfactory fastness properties.

DISCUSSION OF RELATED ART

Coloring systems based on isatin or isatin derivatives offer an alternative solution. Isatin is described in DE-OS 36 35 147 A1 as a substantive dye for coloring keratin fibers either on its own or in conjunction with quinone dyes. Unfortunately, the range of variation of the color tones obtainable is limited. In most cases, a golden color is obtained.

Another isatin-containing coloring system is described in EP 359 465 A2. In this case, the color is obtained with a ketimine (Schiff's base) produced by the reaction of an isatin with an aniline derivative. The ketimine is either applied as such to keratin fibers where it develops color or, alternatively, a mixture consisting of an isatin and an aniline derivative is applied to the fibers and initially forms the ketimine in situ, after which the color develops on the fibers.

EP 497 697 A1 describes hair coloring formulations based on isatins and aminoindoles or indolines containing a primary amino group, Schiff's bases being formed in a condensation reaction.

EP 0 502 783 A1 describes hair coloring formulations containing isatins and aminopyridines or isatins and aminopyrimidines containing a primary amino group.

EP 0 502 784 A1 describes hair coloring formulations containing isatins and substituted diamines or aminophenols or isatins and (bisaryl) alkylenediamines.

DESCRIPTION OF THE INVENTION

It has now surprisingly been found that certain isatin derivatives containing sulfo groups or carboxyl groups are eminently suitable for coloring keratin-containing fibers.

Examples of keratin-containing fibers are wool, furs, skins and human hair. In principle, however, the isatin derivatives containing sulfo or carboxyl groups described in more detail hereinafter may also be used for coloring other natural fibers, for example cotton, jute, sisal, linen or silk, modified natural fibers, for example regenerated cellulose, nitrocellulose, alkyl or hydroxyalkylcellulose or acetyl cellulose and synthetic fibers, for example polyamide, polyacrylonitrile, polyurethane and polyester fibers.

The present invention relates to the use of isatin derivatives corresponding to formula I:

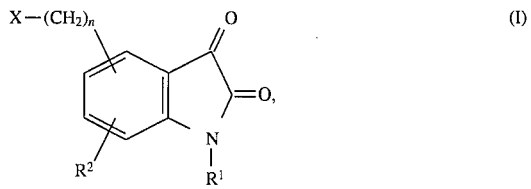

in which $R^1$ is hydrogen, a $C_{1-4}$ alkyl, $C_{2-4}$ hydroxyalkyl, $C_{2-20}$ acyl, benzyl or phenyl group, $R^2$ is hydrogen, a $C_{1-4}$ alkyl, $C_{1-4}$ alkoxy, hydroxy, halogen or nitro group, X is a sulfo group —$SO_3H$ or a carboxyl group —COOH and n is an integer of 0 to 3, and water-soluble salts thereof for coloring keratin-containing fibers.

Examples of water-soluble salts are inter alia the alkali metal or ammonium salts.

Isatin derivatives corresponding to formula I, in which $R^1$ and $R^2$ are hydrogens and in which N=0, i.e. isatin derivatives corresponding to formula I in which the sulfo group or the carboxyl group is directly attached to the aromatic ring, are preferably used for coloring keratin-containing fibers. Isatin-5-sulfonic acid, isatin-4-carboxylic acid and isatin-5-carboxylic acid are most particularly suitable.

The isatin derivatives corresponding to formula I give yellow color tones. The resistance of the colors to washing is surprisingly high despite the presence of the hydrophilic sulfo or carboxyl group. At the same time, greater depths of color are obtained in purely aqueous systems. There is no need to use toxicologically questionable solubilizing agents, such as primary short-chain alcohols for example, although basically their use is not ruled out.

Particularly brilliant colors in the yellow, red and violet ranges with good fastness properties (fastness to light, washing and rubbing) are obtained when the isatin derivatives corresponding to formula I are used together with certain aminofunctional compounds or together with certain indole or indoline derivatives.

Accordingly, the present invention also relates to formulations for coloring keratin-containing fibers containing at least one isatin derivative corresponding to formula I and at least one amino acid or an oligopeptide made up of 2 to 9 amino acids.

Suitable amino acids are any naturally occurring and synthetic amino acids, for example the amino acids obtainable by hydrolysis from vegetable or animal proteins, for example collagen, keratin, casein, elastin, soya protein, wheat gluten or almond protein. Both amino acids showing an acidic reaction and those showing an alkaline reaction may be used.

Suitable oligopeptides are any oligopeptides produced from naturally occurring and synthetic amino acids. The oligopeptides may be naturally occurring or synthetic oligopeptides and also the oligopeptides present in polypeptide or protein hydrolyzates providing they are sufficiently soluble in water for use in the coloring formulations according to the invention. Examples are glutathione and the oligopeptides present in the hydrolyzates of collagen, keratin, casein, elastin, soya protein, wheat gluten or almond protein.

However, amino acids or oligopeptides selected from the group consisting of arginine, cysteine, methionine, proline, tyrosine, valine, glycine, glutamic acid, histidine, aspartic acid, alanine, tryptophane, cystine, lysine, hydroxyproline, leucine, isoleucine, phenyl alanine, 3,4-dihydroxyphenyl alanine, serine, ornithine, threonine, glutathione are particularly suitable for use in the coloring formulations according to the invention.

The present invention also relates to formulations for coloring keratin-containing fibers containing at least one isatin derivative corresponding to formula I and at least one aromatic amine corresponding to formula II:

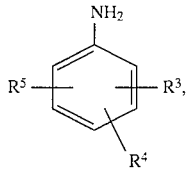
(II)

in which $R^3$, $R^4$ and $R^5$ are hydrogens, $C_{1-4}$ alkyl groups, hydroxy groups, carboxyl groups, sulfo groups, $C_{1-4}$ aminoalkyl groups or $NR^6R^7$ groups, where $R^6$ and $R^7$ independently of one another are hydrogens, $C_{1-4}$ alkyl groups, aryl groups or $C_{2-4}$ hydroxyalkyl groups, with the proviso that at most two of the groups $R^3$, $R^4$ and $R^5$ are simultaneously hydrogens and/or $C_{1-4}$ alkyl groups; two of the groups $R^3$, $R^4$ and $R^5$ together may also form a fused benzene ring optionally substituted by $C_{1-4}$ alkyl, hydroxy, carboxyl, sulfo, $C_{1-4}$ aminoalkyl or amino.

Examples are sulfanilic acid, 1,5-, 1,8-, 2,3-diaminonaphthalene, 6-amino-1-naphthol-3-sulfonic acid, 4-amino-, 4,4'-diaminodiphenylamine, 4,4'-diaminodiphenyl-amine-2-sulfonic acid.

Preferred coloring formulations are those in which the aromatic amine of formula II is selected from the group consisting of p-tolylenediamine, 4-aminophenol, 4-amino-2-aminomethylphenol, 3,4-diaminobenzoic acid, 2,4,5,6-tetraaminobenzene, 1-(β-hydroxyethyl)-2,5-diaminobenzene.

The present invention also relates to formulations for coloring keratin-containing fibers containing at least one isatin derivative corresponding to formula I and at least one aromatic amine corresponding to formula III:

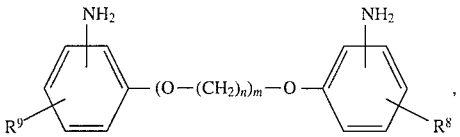
(III)

in which $R^8$ and $R^9$ independently of one another represent hydrogens, $C_{1-4}$ alkyl groups, hydroxy groups or amino groups, n is an integer of 2 to 4 and m is an integer of 1 to 4.

Coloring formulations in which the aromatic amine of formula III is 1,3-bis-(2,4-diaminophenoxy)-propane are preferred.

The present invention also relates to formulations for coloring keratin-containing fibers containing at least one isatin derivative corresponding to formula I and at least one aminopyrimidine corresponding to formula IV:

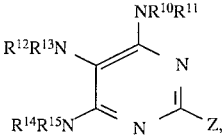
(IV)

in which $R^{10}$, $R^{11}$, $R^{12}$, $R^{13}$, $R^{14}$ and $R^{15}$ independently of one another are hydrogens, $C_{1-4}$ alkyl groups or $C_{2-4}$ hydroxy-alkyl groups and Z is hydrogen, an OH group or an $NR^{16}R^{17}$ group, where $R^{16}$ and $R^{17}$ independently of one another are hydrogens, $C_{1-4}$ alkyl groups or $C_{2-4}$ hydroxyalkyl groups.

Preferred coloring formulations are those in which unsubstituted tetraaminopyrimidine is used.

The present invention also relates to formulations for coloring keratin-containing fibers containing at least one isatin derivative corresponding to formula I and at least one indole derivative corresponding to formula Va:

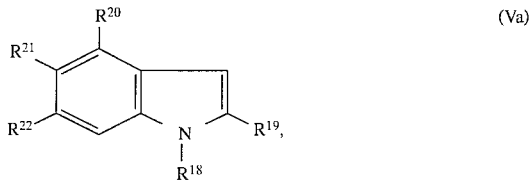
(Va)

in which $R^{18}$ is hydrogen, a $C_{1-4}$ alkyl or $C_{2-4}$ acyl group, $R^{19}$ is hydrogen or a carboxyl group and $R^{20}$, $R^{21}$ and $R^{22}$ are hydrogens, $C_{1-4}$ alkyl groups, $C_{2-4}$ acyloxy groups, hydroxy groups, amino groups or $C_{1-4}$ alkoxy groups, with the proviso that at most two of the groups $R^{20}$, $R^{21}$ and $R^{22}$ are simultaneously hydrogens and/or $C_{1-4}$ alkyl groups, or at least one indoline derivative corresponding to formula Vb:

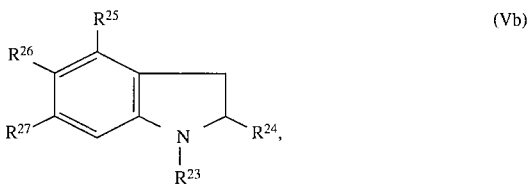
(Vb)

in which $R^{23}$ is hydrogen, a $C_{1-4}$ alkyl or $C_{2-4}$ acyl group, $R^{24}$ is hydrogen or a carboxyl group and $R^{25}$, $R^{26}$ and $R^{27}$ are hydrogens, $C_{1-4}$ alkyl groups, $C_{2-4}$ acyloxy groups, hydroxy groups, amino groups or $C_{1-4}$ alkoxy groups, with the proviso that at most two of the groups $R^{25}$, $R^{26}$ and $R^{27}$ are simultaneously hydrogens and/or $C_{1-4}$ alkyl groups.

Preferred coloring formulations are those in which the indole derivative corresponding to formula Va or the indoline derivative corresponding to formula Vb is selected from the group consisting of 5,6-dihydroxyindole, 5,6-diacetoxyindole, 4-hydroxyindoline, 6-aminoindoline and 5,6-dihydroxyindoline.

All the compounds with a substituted or unsubstituted amino function used in the coloring formulations according to the invention may be used both in free form and in the form of their water-soluble salts. Examples of water-soluble salts are inter alia hydrochlorides, hydrobromides or sulfates.

Several different isatin derivatives corresponding to formula I may also be used together in the coloring formulations according to the invention. Several different amino acids or oligopeptides and several different compounds corresponding to formulae II, III, IV, Va and Vb may also be used together.

The coloring formulations according to the invention give intensive colors at physiologically tolerable temperatures of below 45° C. Accordingly, they are particularly suitable for coloring human hair.

For application to human hair, the coloring formulations according to the invention may be incorporated in a water-containing cosmetic carrier. Suitable water-containing cosmetic carriers are, for example, creams, emulsions, gels or even surfactant-containing foaming solutions, such as shampoos for example, or other preparations which are suitable for application to the hair. The isatins corresponding to formula I and also the amino acids and oligopeptides or the compounds corresponding to formulae II, III, IV, Va and Vb are each present in quantities of 0.01 to 20% by weight and preferably 1 to 7% by weight, based on the coloring preparation as a whole.

The water-containing cosmetic carrier typically contains wetting agents and emulsifiers, such as anionic, nonionic or ampholytic surfactants, for example fatty alcohol sulfates, alkane sulfonates, α-olefin sulfonates, fatty alcohol polyglycol ether sulfates, alkyl glycosides, ethylene oxide adducts with fatty alcohols, with fatty acids, with alkylphenols, with sorbitan fatty acid esters, with fatty acid partial glycerides and fatty acid alkanolamides; thickeners, for example fatty alcohols, fatty acids, paraffin oils, fatty acid esters and other fatty components in emulsified form; water-soluble polymeric thickeners, such as natural gums, for example gum arabic, karaya gum, guar gum, carob bean flour, linseed gums and pectin, biosynthetic gums, for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose, clays, for example bentonite, or fully synthetic hydrocolloids, for examplepolyvinyl alcohol or polyvinyl pyrrolidone, hair-care additives, for example water-soluble cationic polymers, anionic polymers, nonionic polymers, amphoteric or zwitterionic polymers, pantothenic acid, vitamins, plant extracts or cholesterol, pH regulators, complexing agents and perfume oils and also reducing agents for stabilizing the ingredients, for example ascorbic acid. FinaLly, dyes may also be present to color the cosmetic preparations.

The pH value of the read-to-use coloring preparations is between 2 and 11 and preferably between 5 and 9. Where components oxidizable in air, for example 5,6-dihydroxyindole, 5,6-dihydroxyindoline and derivatives thereof, are used, a mildly alkaline pH value of 7 to 11 and preferably 8 to 10 is of advantage.

To color hair, the coloring formulations according to the invention are applied to the hair in the form of the water-containing cosmetic carrier in a quantity of 100 g, left thereon for around 30 minutes and then rinsed out or washed out with a commercial shampoo.

If the coloring formulations according to the invention are used in the form of a water-containing cosmetic preparation, it is of advantage (but not necessary) to package the isatin derivative corresponding to formula I separately from the second reactive component, i.e. the amino acid or the oligopeptide or the compounds corresponding to formulae II, III, IV, Va and Vb.

The two components (isatin derivative of formula I and the second reactive component) may then be applied to the hair either at the same time or even successively. It does not matter which of the two components is applied first. Application of the first component and application of the second component may be separated by a time interval of up to 30 minutes.

However, it is of particular advantage to package all the components together in a water-free powder-form preparation.

Accordingly, the present invention also relates to hair coloring formulations in the form of a powder containing at least one isatin derivative corresponding to formula I in a quantity of 1 to 90% by weight and preferably 20 to 50% by weight and an amino acid or an oligopeptide made up of 2 to 9 amino acids in a quantity of 1 to 90% by weight and preferably 20 to 50% by weight, based on the powder-form coloring formulation as a whole.

Particularly preferred hair coloring formulations are those in which the isatin derivative corresponding to formula I is selected from isatin-5-sulfonic acid, isatin-4-carboxylic acid and isatin-5-carboxylic acid and the amino acid or the oligopeptide is selected from arginine, cysteine, methionine, proline, tyrosine, valine, glycine, glutamic acid, histidine, aspartic acid, alanine, tryptophane, cystine, lysine, hydroxyproline, leucine, isoleucine, phenyl alanine, 3,4-dihydroxyphenyl alanine, serine, ornithine, threonine and glutathione.

The present invention also relates to hair coloring formulations in the form of a powder containing at least one isatin derivative corresponding to formula I in a quantity of 1 to 90% by weight and preferably 20 to 50% by weight and at least one aromatic amine corresponding to formula II in a quantity of 1 to 90% by weight and preferably 20 to 50% by weight, based on the powder-form coloring formulation as a whole.

Particularly preferred hair coloring formulations are those in which the isatin derivative corresponding to formula I is selected from isatin-5-sulfonic acid, isatin-4-carboxylic acid and isatin-5-carboxylic acid and the aromatic amine corresponding to formula II is selected from the group consisting of p-tolylenediamine, 4-aminophenol, 4-amino-2-aminomethylphenol, 3,4-diaminobenzoic acid, 2,4,5,6-tetraaminobenzene, 1-(β-hydroxyethyl)-2,5-diaminobenzene.

The present invention also relates to hair coloring formulations in the form of a powder containing at least one isatin derivative corresponding to formula I in a quantity of 1 to 90% by weight and preferably 20 to 50% by weight and at least one aromatic amine corresponding to formula III in a quantity of 1 to 90% by weight and preferably 20 to 50% by weight, based on the powder-form coloring formulation as a whole.

Particularly preferred hair coloring formulations are those in which the isatin derivative corresponding to formula I is selected from isatin-5-sulfonic acid, isatin-4-carboxylic acid and isatin-5-carboxylic acid and the aromatic amine corresponding to formula III is 1,3-bis-(2,4-diaminophenoxy)-propane.

The present invention also relates to hair coloring formulations in the form of a powder containing at least one isatin derivative corresponding to formula I in a quantity of 1 to 90% by weight and preferably 20 to 50% by weight and at least one aminopyrimidine corresponding to formula IV in a quantity of 1 to 90% by weight and preferably 20 to 50% by weight, based on the powder-form coloring formulation as a whole.

Particularly preferred hair coloring formulations are those in which the isatin derivative corresponding to formula I is selected from isatin-5-sulfonic acid, isatin-4-carboxylic acid and isatin-5-carboxylic acid and the aminopyrimidine corresponding to formula IV is unsubstituted tetraaminopyrimidine.

The present invention also relates to hair coloring formulations in the form of a powder containing at least one isatin derivative corresponding to formula I in a quantity of 1 to 90% by weight and preferably 20 to 50% by weight and at least one indole derivative corresponding to formula Va or one indoline derivative corresponding to formula Vb in a quantity of 1 to 90% by weight and preferably 20 to 50% by weight, based on the powder-form coloring formulation as a whole.

Particularly preferred hair coloring formulations are those in which the isatin derivative corresponding to formula I is selected from isatin-5-sulfonic acid, isatin-4-carboxylic acid and isatin-5-carboxylic acid and the indole derivative corresponding to formula Va or the indoline derivative corresponding to formula Vb are selected from 5,6-dihydroxyindole, 5,6-diacetoxyindole, 4-hydroxyindoline, 6-aminoindoline and 5,6-dihydroxyindoline.

The isatins corresponding to formula I may also advantageously be combined with pyridines such as, for example, 2,6-dihydroxy-3,4-dimethylpyridine, 2-amino-3-hydroxypyridine, 2-methylamino-3-amino-6-methoxypyridine, 3,5-diamino-2,6-dimethoxypyridine as a second component.

In the most simple case, the powder-formhair coloring formulations contain only a water-soluble polymeric thickener besides the two reactive components (isatin derivative corresponding to formula I and amino acid or oligopeptide or compounds corresponding to formulae II, III, IV, Va and Vb). The function of the thickener is to provide the ready-to-use hair coloring preparation obtained after the addition of water with the consistency required for application. Suitable thickeners are, for example, natural gums, for example guar flour, gum arabic, karaya gum, carob bean flour, linseed gums and pectins, biosynthetic gums, such as for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose.

Other optional components in the powder-form hair coloring formulations are metal salts, for example the acetates, sulfates, chlorides, bromides, carbonates, glycolates, lactates or gluconates of the alkali and alkaline earth metals, hair-care additives, for example water-soluble cationic polymers, anionic polymers, amphoteric or zwitterionic polymers, pantothenic acid, vitamins, plant extracts, complexing agents, perfume components and also reducing agents, for example ascorbic acid.

To prepare the ready-to-use hair coloring preparation, 1 to 30 g and preferably 3 to 15 g of the powder are made up to 100 g with hot water (90° to 100° C.). Water/alcohol mixtures or other cosmetically compatible solvents may also be used to dissolve the powder.

After cooling to around 40° C., the ready-to-use hair coloring preparation is applied to the hair and left thereon for 30 minutes. The hair is then rinsed or washed with a commercial hair shampoo.

The following Examples are intended to illustrate the invention without limiting it in any way.

Examples

Example I

A hair coloring emulsion with the following composition was prepared:

| | |
|---|---|
| $C_{16/18}$ fatty alcohol | 8.5 g |
| $C_{12/14}$ fatty alcohol ether sulfate (28%), Na salt | 25 g |
| Isatin-5-sulfonic acid | 1 g |
| Water | ad 100 g |
| $NH_3$ | to pH 9.0 |

The hair coloring emulsion was applied to approximately 5 cm long strands of standardized, 90% grey human hair and left thereon for 30 minutes at 32° C. On completion of the coloring process, the hair was rinsed, washed with a standard shampoo and dried. A straw yellow color tone with a fastness to light of 3.0 according to DIN 54004 was obtained.

Under the same conditions, a hair coloring emulsion in which isatin was used instead of isatin-5-sulfonic acid produced a tone with a fastness to light of only 2.0 according to DIN 54004.

[DIN 54004 stands for "Deutsche Industrie-Norm 54004", Testing of Textiles for Fastness to Color, Determining the Fastness to Light of Colors and Prints Using Artificial Daylight; April 1966 Edition. The standards are sold exclusively through Beuth-Vertrieb GmbH, Berlin 30 and Cologne, Germany. The measuring arrangement and test procedure are described in detail in the standard.]

Example II

Powder-form hair coloring formulations with compositions 1 to 12 were prepared (see Table 1: quantities in g).

| Formulation No. | 1 | 2 | 3 | 4 | 5 | 6 | 7 | 8 | 9 | 10 | 11 | 12 |
|---|---|---|---|---|---|---|---|---|---|---|---|---|
| Guar flour (Emulkoll 35) Lucas Meyer) | 1.0 | 1.0 | 1.0 | 1.0 | 1.0 | 1.0 | 1.0 | 1.0 | 1.0 | 1.0 | 1.0 | 1.0 |
| Sodium acetate.$3H_2O$ | 1.4 | 1.4 | 1.4 | 1.4 | 1.4 | 1.4 | 1.4 | 1.4 | 1.4 | 1.4 | 1.4 | 1.4 |
| Isatin-5-sulfonic acid, Na salt | 2.5 | 2.5 | 2.5 | 2.5 | 2.5 | 2.5 | 2.5 | 2.5 | 2.5 | — | — | 2.5 |
| Isatin-4-carboxylic acid | — | — | — | — | — | — | — | — | — | 1.9 | 1.9 | — |
| 2,5-diaminotoluene sulfate | 2.2 | — | — | — | — | — | — | 2.2 | — | — | — | — |
| 1-(β-hydroxyethyl)-2,5-diaminobenzene sulfate | — | 2.5 | — | — | — | — | — | 2.5 | — | — | — | — |
| Tetraaminopyrimidine sulfate | — | — | 2.6 | — | — | — | — | — | — | — | — | — |
| 4-Aminophenol hydrochloride | — | — | — | 1.4 | — | — | — | — | — | — | — | — |
| 4-Amino-2-aminomethylphenol hydrochloride | — | — | — | — | 2.1 | — | — | 2.1 | — | — | 2.1 | — |
| 3,4-Diaminobenzoic acid | — | — | — | — | — | 1.5 | — | — | — | — | — | — |
| 1,3-Bis-(2,4-diaminophenoxy)-propane tetrahydrochloride | — | — | — | — | — | — | 4.4 | — | — | — | — | — |
| 5,6-Dihydroxyindoline hydrobromide | — | — | — | — | — | — | — | — | 2.3 | — | — | — |
| 2,4,5,6-tetraaminobenzene tetrahydrochloride | — | — | — | — | — | — | — | — | — | 2.8 | — | — |
| L-Arginine | — | — | — | — | — | — | — | — | — | — | — | 1.8 |

To prepare ready-to-use hair coloring preparations, compositions 1 to 12 were made up to 100 g with hot water (90° to 100° C.) and the pH value was adjusted to 9.0 with $Na_2CO_3$. After cooling to around 40° C., the ready-to-use preparations were applied to strands of light blond natural hair. The strands were then wrapped in aluminium foil and left in a drying cabinet for 30 minutes at 32° C. They were then shampooed, washed and dried.

The color tones obtained are shown in Table 2:

| Example No. | Color |
|---|---|
| 1 | Cherry red |
| 2 | Cherry red |
| 3 | Cinnabar red |
| 4 | Yellowish copper |
| 5 | Yellowish copper |
| 6 | Neutral yellow |
| 7 | Medium blond |
| 8 | Reddish copper |

| Example No. | Color |
|---|---|
| 9 | Reddish brown |
| 10 | Violet-red |
| 11 | Red-brown |
| 12 | Pink-colored |

The colors are extremely to fast to washing.

Example III

A hair coloring gel with the following composition

| | |
|---|---|
| Guar flour | 1.0 g |
| 5,6-Diacetoxyindole | 2.3 g |
| Sodium acetate.3H$_2$O | 1.4 g |
| Water | ad 100 g |
| NH$_2$CO$_3$ | to pH 9.0 |

This hair coloring gel was applied to strands of light blond natural hair. The strands were left in a drying cabinet for 30 minutes at 32° C. and were then shampooed and washed. A ready-to-use hair coloring gel with composition No. 1 was then applied to the strands, the strands were wrapped in aluminium foil and then left in a drying cabinet for 30 minutes at 32° C. The strands were then shampooed, washed and dried. A brown-red color tone was obtained.

In a second coloring test, a ready-to-use hair coloring gel with composition No. 4 was applied to strands of light blond natural hair, after which the strands were wrapped in aluminium foil, left in a drying cabinet for 30 minutes at 32° C., shampooed and washed. The above-mentioned hair coloring gel of composition A was then applied, after which the strands were left in a drying cabinet for 30 minutes at 32° C., shampooed, washed and dried. A dark copper color tone was obtained.

Example IV

A suspension of 10 mmoles of an isatin corresponding to formula I and 10 mmoles of a second component in 100 ml of water was prepared. The suspension was heated to boiling temperature and filtered after cooling. The pH value was then adjusted to 6. Strands of 90% grey, but non-pretreated human hair were then placed in this coloring solution for 30 minutes at 35° C. and 23° C. The particular coloring temperatures, coloring times, color tones and depths of color are shown in Table 3.

Depth of color was evaluated on the following scale:

−: Very pale color, if any (+): Weak intensity

+: Medium intensity

+(+): Medium to strong intensity

++: Strong intensity

++(+): Strong to very strong intensity

+++: Very strong intensity

TABLE 3

| Coloring with isatin-5-sulfonic acid, Na salt | | | |
|---|---|---|---|
| Second component | Color tone | Coloring temperature | Dept of color |
| 2,3-Diaminonaphthalene | Yellow | 35° C. | ++(+) |
| 1,8-Diaminonaphthalene | Light brown | 35° C. | +(+) |
| 1,5-Diaminonaphthalene | Mid brown | 35° C. | ++ |
| 6-Amino-1-naphthol-3-sulfonic acid | Light brown | 35° C. | ++ |
| N-Phenyl-p-phenylenediamine.HCl | Red-violet | 35° C. | +++ |
| 4,4'-Diaminodiphenylamine.H$_2$SO$_4$ | Blue-violet | 35° C. | +++ |
| 4,4'-Diaminodiphenylamine-2-sulfonic acid | Red-Violet | 35° C. | +(+) |
| 2,5-Diaminotoluene.H$_2$SO$_4$ | Violet-brown | 23° C. | ++ |
| 2,4,5,6-Tetraaminopyrimidine.H$_2$SO$_4$ | Violet-red | 23° C. | ++ |
| 3,4-Diaminobenzoic acid | Yellow-blond | 23° C. | ++ |
| 4-(4-Amino-m-toluidino)-phenol | Dark violet | 30° C. | +++ |
| 3,5-Diamino2,6-dimethoxypyridine | Dark grey-blue | 30° C. | ++(+) |

We claim:

1. A composition for coloring keratin-containing fibers comprising:

(a) at least one isatin derivative corresponding to formula I:

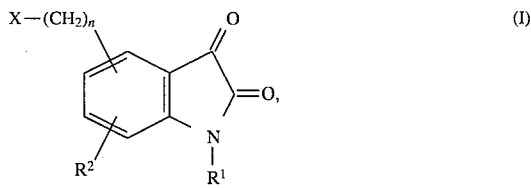

wherein R$^1$ is hydrogen, a C$_{1-4}$ alkyl group, C$_{2-4}$ hydroxyalkyl group, C$_{2-20}$acyl group, a benzyl or phenyl group, R$^2$ is hydrogen, a C$_{1-4}$ alkyl group, C$_{1-4}$ alkoxy group, a hydroxy, halogen or nitro group, X is a sulfo group —SO$_3$H or a carboxyl group —COOH and n is an integer from 0 to 3, including water-soluble salts thereof; and (b) a compound selected from the group consisting of (i) at least one amino acid, (ii) an oligopeptide having from 2 to 9 amino acids, (iii) an aromatic amine corresponding to formula II:

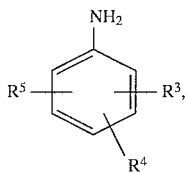

wherein $R^3$, $R^4$ and $R^5$ are hydrogen, $C_{1-4}$ alkyl groups, hydroxy groups, carboxyl groups, sulfo groups, $C_{1-4}$ aminoalkyl groups or $NR^6R^7$ groups, wherein $R^6$ and $R^7$ independently of one another are hydrogen, $C_{1-4}$ alkyl groups, aryl groups or $C_{2-4}$ hydroxyalkyl groups, with the proviso that at most two of the groups $R^3$, $R^4$ and $R^5$ are simultaneously hydrogen or $C_{1-4}$ alkyl groups; and wherein two of the groups $R^3$, $R^4$ and $R^5$ together may also form a fused benzene ring optionally substituted by a $C_{1-4}$ alkyl group, hydroxy group, carboxyl group, sulfo group, $C_{1-4}$ aminoalkyl group or amino group, (iv) an aromatic amine corresponding to formula III:

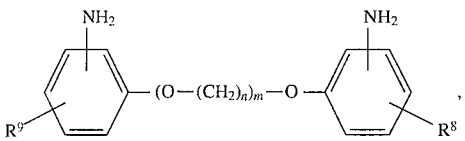

wherein $R^8$ and $R^9$ independently of one another represent hydrogen, $C_{1-4}$ alkyl groups, hydroxy groups or amino groups, n is an integer of 2 to 4 and m is an integer of 1 to 4, (v) at least one aminopyrimidine corresponding to formula (IV):

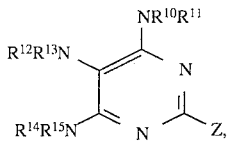

wherein $R^{10}$, $R^{11}$, $R^{12}$, $R^{13}$, $R^{14}$ and $R^{15}$ independently of one another are hydrogen, $C_{1-4}$ alkyl groups or $C_{2-4}$ hydroxyalkyl groups and Z is hydrogen, an OH group or an $NR^{16}R^{17}$ group, wherein $R^{16}$ and $R^{17}$ independently of one another are hydrogen, $C_{1-4}$ alkyl groups or $C_{2-4}$ hydroxyalkyl groups, (vi) at least one indole derivative corresponding to general formula (V):

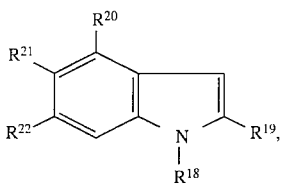

wherein $R^{18}$ is hydrogen, a $C_{1-4}$ alkyl group or $C_{2-4}$ acyl group, $R^{19}$ is hydrogen or a carboxyl group and $R^{20}$, $R^{21}$ and $R^{22}$ are hydrogen, $C_{1-4}$ alkyl groups, $C_{2-4}$ acyloxy groups, hydroxy groups, amino groups or $C_{1-4}$ alkoxy groups, with the proviso that at most two of the groups $R^{20}$, $R^{21}$ and $R^{22}$ are simultaneously hydrogen $C_{1-4}$ alkyl groups, and (vii) at least one indoline derivative corresponding to general formula (VI):

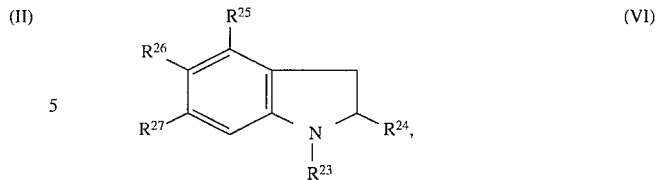

wherein $R^{23}$ is hydrogen, a $C_{1-4}$ alkyl group or $C_{2-4}$ acyl group, $R^{24}$ is hydrogen or a carboxyl group and $R^{25}$, $R^{26}$ and $R^{27}$ are hydrogen, $C_{1-4}$ alkyl groups, $C_{2-4}$ acyloxy groups, hydroxy groups, amino groups or $C_{1-4}$ alkoxy groups, with the proviso that at most two of the groups $R^{25}$, $R^{26}$ and $R^{27}$ are simultaneously hydrogen $C_{1-4}$ alkyl groups.

2. The composition of claim 1 wherein said compound (b)(i) and said compound (b)(ii) are selected from the group consisting of arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine, glutathione, and mixtures thereof.

3. The composition of claim 1 wherein said aromatic amine of formula II is selected from the group consisting of p-tolylenediamine, 4-aminophenol, 4-amino-2-aminomethylphenol, 3,4-diaminobenzoic acid, 2,4,5,6-tetraaminobenzene, and 1-(β-hydroxyethyl)-2,5-diaminobenzene.

4. The composition of claim 1 wherein said aromatic amine of formula III comprises 1,3-bis-(2,4-diaminophenoxy)-propane.

5. The composition of claim 1 wherein in said aminopyrimidine of formula IV $R^{10}$ to $R^{17}$ are hydrogen.

6. The composition of claim 1 wherein said indole derivative of formula V and said indoline derivative of formula VI are selected from the group consisting of 5,6-dihydroxyindole, 5,6-diacetoxyindole, 4-hydroxyindoline, 6-aminoindoline and 5,6-dihydroxyindoline.

7. The composition of claim 1 wherein said isatin derivative (a) is present in an amount of from 1 to 90% by weight, and said compound (b)(i) or (b)(ii) is present in an amount of from 1 to 90% by weight, based on the weight of said composition in powder form.

8. The composition of claim 7 wherein said isatin derivative (a) is selected from the group consisting of isatin-5-sulfonic acid, isatin-4-carboxylic acid and isatin-5-carboxylic acid, and said compound (b)(i) or (b)(ii) is selected from the group consisting of arginine, cysteine, methionine, proline, tyrosine, valine, glycine, glutamic acid, histidine, aspartic acid, alanine, tryptophan, cystine, lysine, hydroxyproline, leucine, isoleucine, phenyl alanine, 3,4-dihydroxyphenyl alanine, serine, ornithine, threonine and glutathione.

9. The composition of claim 1 wherein said isatin derivative (a) is present in an amount of from 1 to 90% by weight, and said compound (b)(iii) is present in an amount of from 1 to 90% by weight, based on the weight of said composition in powder form.

10. The composition of claim 9 wherein said isatin derivative (a) is selected from the group consisting of isatin-5-sulfonic acid, isatin-4-carboxylic acid and isatin-5-carboxylic acid, and said compound (b)(iii) is selected from the group consisting of p-tolylenediamine, 4-aminophenol, 4-amino-2-aminomethylphenol, 3,4-diaminobenzoic acid, 2,4,5,6-tetraaminobenzene, and 1-(β-hydroxyethyl)-2,5-diaminobenzene.

11. The composition of claim 1 wherein said isatin derivative (a) is present in an amount of from 1 to 90% by weight, and said compound (b)(iv) is present in an amount of from 1 to 90% by weight, based on the weight of said composition in powder form.

12. The composition of claim 11 wherein said isatin derivative (a) is selected from the group consisting of isatin-5-sulfonic acid, isatin-4-carboxylic acid and isatin-5-carboxylic acid, and said compound (b)(iv) comprises 1,3-bis-(2,4-diaminophenoxy)-propane.

13. The composition of claim 1 wherein said isatin derivative (a) is present in an amount of from 1 to 90% by weight, and said compound (b)(v) is present in an amount of from 1 to 90% by weight, based on the weight of said composition in powder form.

14. The composition of claim 13 wherein said isatin derivative (a) is selected from the group consisting of isatin-5-sulfonic acid, isatin-4-carboxylic acid and isatin-5-carboxylic acid, and said compound (b)(v) is an unsubstituted tetraaminopyrimidine.

15. The composition of claim 1 wherein said isatin derivative (a) is present in an amount of from 1 to 90% by weight, and said compound (b)(vi) or said compound (b)(vii) is present in an amount of from 1 to 90% by weight, based on the weight of said composition in powder form.

16. The composition of claim 15 wherein said isatin derivative (a) is selected from the group consisting of isatin-5-sulfonic acid, isatin-4-carboxylic acid and isatin-5-carboxylic acid, and said compound (b)(vi) or (b)(vii) is selected from the group consisting of 5,6-dihydroxyindole, 5,6-diacetoxyindole, 4-hydroxyindoline, 6-aminoindoline and 5,6-dihydroxyindoline.

17. A process for coloring keratin-containing fibers comprising contacting said fibers with a composition comprising an isatin derivative corresponding to formula I:

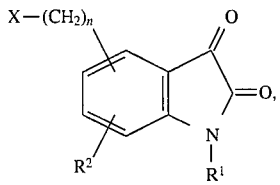

wherein $R^1$ is hydrogen, a $C_{1-4}$ alkyl group, a $C_{2-4}$ hydroxyalkyl group, $C_{2-20}$ acyl group, a benzyl or phenyl group, $R^2$ is hydrogen, a $C_{1-4}$ alkyl group, a $C_{1-4}$ alkoxy group, a hydroxy, halogen or nitro group, X is a sulfo group —$SO_3H$ or a carboxyl group —COOH and n is an integer from 0 to 3, including water-soluble salts thereof.

18. The process of claim 17 wherein in formula I, $R^1$ and $R^2$ are hydrogen and n is 0.

19. The process of claim 17 wherein said isatin derivative is selected from the group consisting of isatin-5-sulfonic acid, isatin-4-carboxylic acid and isatin-5-carboxylic acid.

20. The process of claim 17 wherein said composition further contains a compound selected from the group consisting of (i) at least one amino acid, (ii) an oligopeptide having from 2 to 9 amino acids, (iii) an aromatic amine corresponding to formula II:

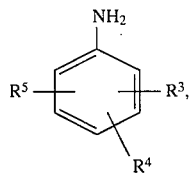

wherein $R^3$, $R^4$ and $R^5$ are hydrogens, $C_{1-4}$ alkyl groups, hydroxy groups, carboxyl groups, sulfo groups, $C_{1-4}$ aminoalkyl groups or $NR^6R^7$ groups, wherein $R^6$ and $R^7$ independently of one another are hydrogen, $C_{1-4}$ alkyl groups, aryl groups or $C_{2-4}$ hydroxyalkyl groups, with the proviso that at most two of the groups $R^3$, $R^4$ and $R^5$ are simultaneously hydrogen or $C_{1-4}$ alkyl groups; and wherein two of the groups $R^3$, $R^4$ and $R^5$ together may also form a fused benzene ring optionally substituted by a $C_{1-4}$ alkyl group, hydroxy group, carboxyl group, sulfo group, $C_{1-4}$ aminoalkyl group or amino group, (iv) an aromatic amine corresponding to formula III:

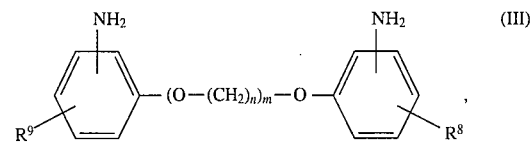

wherein $R^8$ and $R^9$ independently of one another represent hydrogen, $C_{1-4}$ alkyl groups, hydroxy groups or amino groups, n is an integer of 2 to 4 and m is an integer of 1 to 4, (v) at least one aminopyrimidine corresponding to formula (IV):

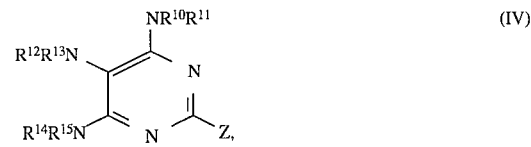

wherein $R^{10}$, $R^{11}$, $R^{12}$, $R^{13}$, $R^{14}$ and $R^{15}$ independently of one another are hydrogen, $C_{1-4}$ alkyl groups or $C_{2-4}$ hydroxyalkyl groups and Z is hydrogen, an OH group or an $NR^{16}R^{17}$ group, wherein $R^{16}$ and $R^{17}$ independently of one another are hydrogen, $C_{1-4}$ alkyl groups or $C_{2-4}$ hydroxyalkyl groups, (vi) at least one indole derivative corresponding to formula (v):

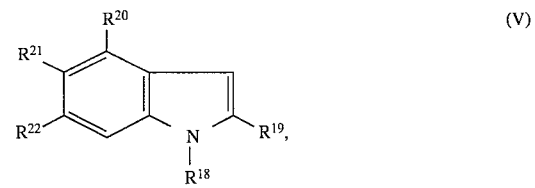

wherein $R^{18}$ is hydrogen, a $C_{1-4}$ alkyl group or a $C_{2-4}$ acyl group, $R^{19}$ is hydrogen or a carboxyl group and $R^{20}$, $R^{21}$ and $R^{22}$ are hydrogen, $C_{1-4}$ alkyl groups, $C_{2-4}$ acyloxy groups, hydroxy groups, amino groups or $C_{1-4}$ alkoxy groups, with the proviso that at most two of the groups $R^{20}$, $R^{21}$ and $R^{22}$ are simultaneously hydrogen or $C_{1-4}$ alkyl groups, (vii) at least one indoline derivative corresponding to formula (VI):

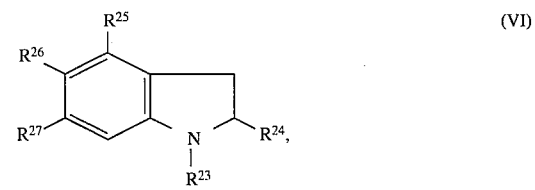

wherein $R^{23}$ is hydrogen, a $C_{1-4}$ alkyl group or a $C_{2-4}$ acyl group, $R^{24}$ is hydrogen or a carboxyl group and $R^{25}$, $R^{26}$ and $R^{27}$ are hydrogen, $C_{1-4}$ alkyl groups, $C_{2-4}$ acyloxy groups, hydroxy groups, amino groups or $C_{1-4}$ alkoxy groups, with the proviso that at most two of the groups $R^{25}$, $R^{26}$ and $R^{27}$ are simultaneously hydrogen or $C_{1-4}$ alkyl groups.

* * * * *